United States Patent [19]

Messinger

[11] Patent Number: 5,048,537
[45] Date of Patent: Sep. 17, 1991

[54] METHOD AND APPARATUS FOR SAMPLING BLOOD

[75] Inventor: Phillip D. Messinger, Powell, Ohio

[73] Assignee: Medex, Inc., Hilliard, Ohio

[21] Appl. No.: 524,224

[22] Filed: May 15, 1990

[51] Int. Cl.⁵ ............................................. A61B 5/02
[52] U.S. Cl. .................................... 128/673; 128/760; 604/52
[58] Field of Search ............... 128/760, 672, 673, 675, 128/692; 604/52, 53, 181, 187, 141, 142

[56] References Cited

U.S. PATENT DOCUMENTS

| | | | |
|---|---|---|---|
| 3,057,350 | 10/1962 | Cowley | 604/248 |
| 4,219,021 | 8/1980 | Fink | 604/93 |
| 4,300,572 | 11/1981 | Knighton | 128/674 |
| 4,763,648 | 8/1988 | Wyatt | 128/673 |
| 4,830,013 | 5/1989 | Maxwell | 128/637 |
| 4,865,583 | 9/1989 | Tu | 604/53 |
| 4,981,140 | 1/1991 | Wyatt | 128/673 |
| 5,002,066 | 3/1991 | Simpson et al. | 128/760 |

OTHER PUBLICATIONS

Baxter, VAMP TM Venous/Arterial Blood Management Protection System (prior to) 5/90.
Spectramed—DTX/Plus TM Disposable Transducer Kit Instructions (3 pages) (prior to) 5/90.

Primary Examiner—Max Hindenburg
Assistant Examiner—James M. Boler
Attorney, Agent, or Firm—Wood, Herron & Evans

[57] ABSTRACT

A source of saline solution under pressure is connected through tubing to a catheter inserted in a patient's blood vessel. A waste collection bag is connected to the tubing through a stopcock which permits the selective connecting of the catheter to the waste collection bag or the bag of saline solution. The sampling site is in the tubing between the catheter and the stopcock. Normally, saline solution flows into the patient's blood vessel. When a sample is to be taken, the stopcock is shifted so that the pressure of the patient's blood forces blood into the tubing, driving saline into the waste collection bag. When blood has reached the sampling site, blood is extracted with a hypodermic syringe.

5 Claims, 1 Drawing Sheet

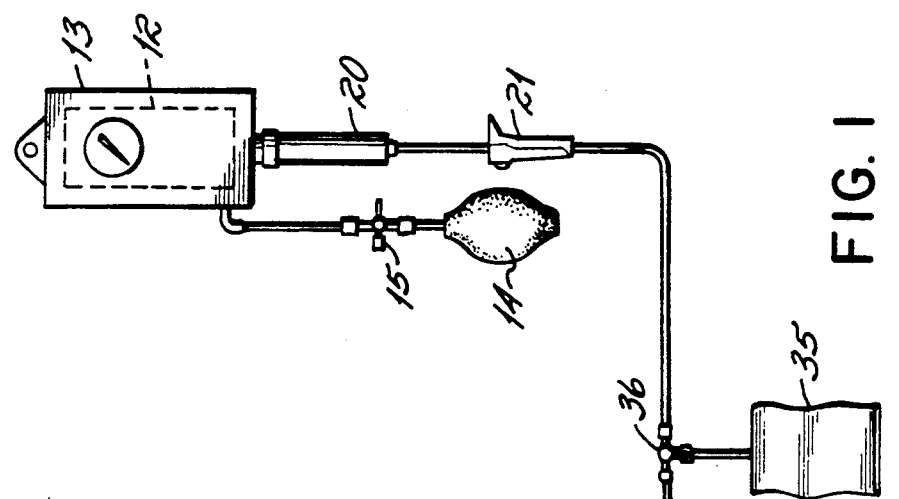
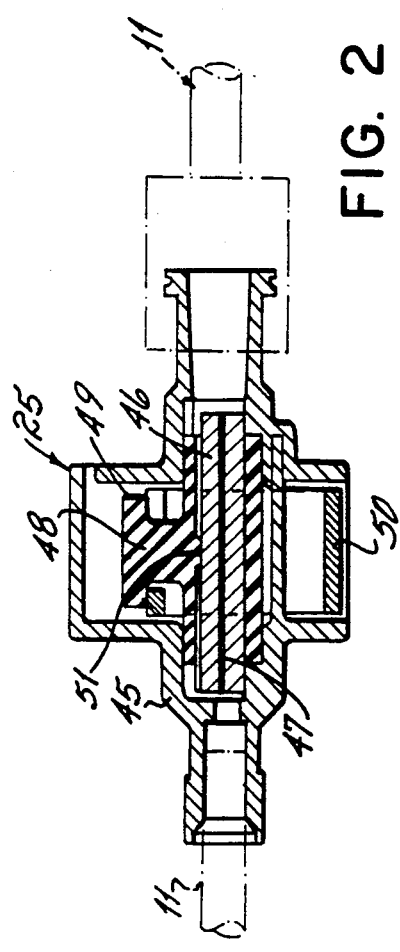
FIG. 1
FIG. 2

METHOD AND APPARATUS FOR SAMPLING BLOOD

This invention relates to blood pressure monitoring apparatus, and particularly the invention relates to apparatus for removing samples of a patient's blood during a blood pressure monitoring procedure.

BACKGROUND OF THE INVENTION

Blood pressure monitoring apparatus is well known. It includes a catheter inserted into a patient's blood vessel, a tube connecting the catheter to a transducer, a supply of saline solution connected through the transducer to the catheter and a flush valve connected in the line to the catheter. The system through the catheter is filled with the saline solution, the saline solution forming a static column whereby variations in blood pressure are communicated is monitored in real time. The flush valve has a capillary through which the saline solution flows, very slowly, to the patient. The slow dripping of the saline solution prevents any clotting of blood in the catheter which might introduce an error into the monitoring of the blood pressure. The flush valve contains a bypass by which a rapid flow of saline solution can be introduced into the system as needed.

It has been conventional to provide a site for withdrawing a blood sample. A stopcock is placed in series between the catheter and the transducer. The stopcock has a port that is normally closed by a solid plug (dead ender). The procedure for drawing a blood sample through the free port on the stopcock has required the following major steps: The stopcock is shifted to block flow of saline solution from the supply and open ports between the catheter and the plugged port. The dead ender plug is removed and carefully set aside to avoid contamination. A syringe is inserted in the opening created by the removal of the dead ender and about 3-5 cc mixture of blood and saline is withdrawn to remove the saline from the catheter and tube leading to the stopcock so that only whole blood is present at the free port of the stopcock. A heparinized syringe is inserted into the free stopcock port to withdraw about 1 or more cc of blood. The stopcock is shifted to open the free port to the saline supply and block the port to the catheter. The free port is flushed, using the flush valve, with saline and the dead ender is replaced. The stopcock is then shifted again to block the free port and connect the catheter to the saline supply. The flush valve then flushes the blood out of the tube and catheter, whereupon the system between the catheter and transducer is filled and ready for resumption of normal monitoring operation.

The foregoing procedure has obvious disadvantages. A number of manipulative steps are required to obtain the blood sample. A number of chances for contamination of the patient's blood are presented in the opening of the port to bring the blood to the stopcock for sampling. Blood usually drips from the sampling port. The exposure of attending people to the patient's blood is a matter of considerable concern because of the possibility of spreading AIDS, hepatitis and the like.

In copending application Ser. No. 07/288,568, filed Dec. 22, 1988, an improved sampling system is disclosed. There, a T-connection is connected to the tubing between the saline source and the catheter via a stopcock. The T-connection has an antiseptic syringe on one port and a sampling site on the other port. The antiseptic syringe is used to draw saline or a combination of saline and blood into the syringe until the liquid at the sampling site is pure blood. Thereafter, a hypodermic syringe is employed to withdraw blood from the sampling site. The antiseptic syringe thereafter returns the saline to the system.

BRIEF SUMMARY OF THE INVENTION

The objective of the present invention has been to provide an improved system for taking samples of blood and specifically a system that does not require any syringe to pull saline solution and blood to the sampling site.

The objective of the invention is achieved by the mounting of a flexible waste collection bag by means of a stopcock to the tubing between the pressurized saline bag and the catheter. A sampling site is mounted in the tubing between the catheter and the stopcock.

The bag of saline solution is normally pressurized to about 300 mmHg. The patient's internal cardiovascular system is pressurized normally at about 100 mmHg. The flexible collection bag in the beginning is at about 0 mmHg relative to atmospheric pressure and never exceeds a pressure of about 30 mmHg. By shifting the stopcock from normal operation wherein 300 mmHg is forcing saline solution into the patient's blood vessel, to sampling operation connecting the patient to the collection bag, the patient's cardiovascular system at 100 mmHg pumps blood towards the waste collection bag.

Thus, there is no need for the attendant to manipulate a syringe to withdraw saline in order to bring blood to a sampling site. Rather, the pressure in the patient's blood vessel pumps the saline into the waste collection bag until blood in the tubing reaches the sampling site.

The closed system of the present invention allows the attendant to perform the following operations:

(a) Infuse needed fluids into patient.
(b) Monitor patient's blood pressure.
(c) Pump blood from the patient towards the waste collection bag to move blood to a sampling site.
(d) Collect waste fluids in a separate collection bag.
(e) Adjust the rate that blood enters or leaves the system.
(f) Return unused blood to the patient.

All of the foregoing functions can be performed without any blood or fluids contacting the outside environment.

BRIEF DESCRIPTION OF THE DRAWINGS

The several features and objectives of the present invention will become more readily apparent from the following detailed description taken in conjunction with the accompanying drawings in which:

FIG. 1 is a diagrammatic view of the closed blood sampling system; and

FIG. 2 is an enlarged cross-sectional view of a flush device employed in the system.

DETAILED DESCRIPTION OF THE DRAWINGS

Referring to FIG. 1, there is disclosed a catheter 10 for insertion into a patient's blood vessel. The catheter 10 is connected by transparent tubing 11 to a bag 12 of saline solution. The bag 12 is wrapped in a pressure cuff 13 that can be inflated by an inflation squeeze bulb 14 through a stopcock 15. The pressure cuff 13 is of the type disclosed in U.S. Pat. No. 4,551,136, which disclosure is fully incorporated herein by reference. It wraps about a bag of saline solution 12 and is inflatable to pressurize the bag of saline solution, normally to a pressure of about 300 mmHg.

The bag 12 is connected to the transparent tubing 11 by a conventional drip chamber 20. A roller clamp 21 is mounted on the tubing adjacent the drip chamber 20 in order to selectively block the flow of saline from the bag toward the patient. The tubing contains a flush device 25 as depicted in FIG. 2 and will be described in greater detail below. Its function is to restrict flow of saline to the patient in the normal operation to approximately 3 cc of saline per hour. The flush device 25 has a parallel passage that permits flow to increase (adjustably) to approximately 120 cc per minute. A transducer 26 is mounted in the tubing between the flush device 25 and the catheter 10 and is electrically connected to a monitor 27 by a cable 28 for monitoring the patient's blood pressure. A transducer of the type disclosed in U.S. Pat. No. 4,920,972, fully incorporated herein by reference, can be employed. A three-way stopcock 29 is connected between the transducer 26 and the catheter 10 and is normally used for an initial connection of the system to atmospheric pressure to zero the monitor 27. Thereafter, it remains set to permit flow to the patient.

The system thus far described is, in general, a conventional system for providing the continuous monitoring of a patient's blood pressure. The invention consists of the connecting to that system of a waste collection bag 35 by means of a shunted stopcock 36. The shunted stopcock 36 has two positions. In one position, flow is permitted from the saline bag 12 to the catheter 10. In the other position, flow is permitted from the catheter 10 to the waste collection bag 35.

A blood sampling site 38 is connected between the transducer 26 and the catheter 10. The sampling site is a T-connection that is connected in series with the tubing 11 and has a port 39 that is closed by a plug which can be penetrated by a hypodermic needle. A hypodermic syringe 40 is connected to the site when a blood sample is to be taken.

The flush device 25 may be of the type depicted in FIG. 2. It is connected in series with the tubing 11. It has a housing 45 in which is mounted a marine capillary tube 46 having a very small bore 47. The small bore permits a flow of about 3 cc per hour when the saline solution is pressurized to 300 mmHg. Surrounding the capillary tube is an elastic pull tube 48 having a flanged knob 49. A push button 50, connected to the knob 49, will, when pushed, stretch the elastic pull tube 48, pulling it away from the capillary tube by the flanged knob 49. The pull tube has a dam 51 which normally blocks flow of fluid around the capillary tube 46, thus forcing the fluid through the capillary tube 46. However, when the push button is depressed to create the flush condition, the fluid flows rapidly, up to 120 cc per minute around the capillary tube. That volume per minute can be controlled by the distance the push button 50 is depressed.

In the operation of the invention, the bag of saline 12 under pressure is connected to the tubing 11. The flush device 25 is operated in the flush mode to cause the whole system to fill with saline solution and to drive air out of the system. The button 50 of the flush device is released and the catheter is then inserted into the patient's blood vessel.

In this condition of normal operation, saline solution slowly drips into the patient's blood vessel in order to prevent clotting of the blood around the catheter 10. The saline solution in the tube 11 presents an essentially static column that conveys the patient's blood pressure to the transducer 26. Its fluctuations are monitored in real time by the monitor 27.

From time to time, it is desired to take a blood sample from the patient. To take the blood sample, the shunted stopcock 36 is turned to the position blocking the saline solution from pressurized bag 12 and opening the passage from the catheter 10 to the collection bag 35. The attendant then manipulates the flush device 25 to permit the blood pressure in the patient's cardiovascular system, nominally at 100 mmHg, to pump blood into the tubing 11. The introduction of blood into the tubing 11 drives saline solution into the bag 35, the bag 35 initially being at 0 mmHg. The pressure in the bag will never increase beyond about 30 mmHg and thus the patient always has the pressure to drive the saline into the bag. The attendant observes the movement of blood in the catheter from the transparent tubing 11 until the blood has passed the sampling site 38. At that point, the flush passage is closed. The syringe 40 is applied to the sampling site to withdraw sufficient blood for the laboratory testing. That sampling operation having been completed, the attendant reverses the position of the shunted stopcock 36 so that the pressurized source of saline again is connected to the catheter. The attendant then opens the flush device to rapidly drive the patient's blood back into the patient's body. As soon as that is accomplished, the flush device is released and flow through the capillary tube is resumed.

From the above disclosure of the general principles of the present invention and the preceding detailed description of a preferred embodiment, those skilled in the art will readily comprehend the various modifications to which the present invention is susceptible. Therefore, I desire to be limited only by the scope of the following claims and equivalents thereof:

I claim:

1. A blood sampling system comprising:
   a catheter for insertion into a patient's blood vessel that has a nominal pressure of about 100 mmHg,
   a source of saline solution pressurized to about 300 mmHg,
   tubing connecting said source to said catheter,
   a stopcock in series with said tubing,
   a waste collection bag connected to said stopcock,
   and a sampling site in said tubing between said catheter and said stopcock,
   whereby said saline solution source may be blocked and said catheter placed in communication with said collection bag to enable the pressure in the patient's blood vessel to drive saline solution from said tubing into said waste collection bag and to drive said blood from the blood vessel at least to said sampling site.

2. The system as in claim 1 further comprising
   a flush device connected in series in said tubing between said sampling site and said collection bag,
   said flush device having a restricted passage to permit saline to pass slowly to said patient and a normally closed parallel passage permitting rapid flow through said flush device, and means for temporarily opening said parallel passage to speed flow of saline into said collection bag.

3. A blood sampling system as in claim 1 wherein said stopcock is a two-way stopcock permitting flow selectively between said source of saline solution and said catheter; and between said catheter and said collection bag.

4. A system as in claim 1 in which said collection bag has a capacity several times greater than the volume in said tubing between said catheter and said sampling site, whereby one waste collection bag can be used for several samplings without being removed.

5. In a blood pressure monitoring system, having a bag of saline solution pressurized to about 300 mmHg, a catheter for insertion into a patient's blood vessel which is at a nominal pressure of about 100 mmHg, and tubing connecting said bag to said catheter, the method of obtaining a blood sample, comprising the steps of:

connecting a low pressure bag to said tubing, blocking flow of saline from said pressurized bag of saline, permitting the patient's blood vessel to pump saline from said catheter through said tubing to said low pressure bag to partially fill said tubing with blood, and extracting a blood sample from that portion of said tubing that is filled with blood.

* * * * *

UNITED STATES PATENT AND TRADEMARK OFFICE
CERTIFICATE OF CORRECTION

PATENT NO. : 5,048,537
DATED : September 17, 1991
INVENTOR(S) : Phillip D. Messinger It is certified that error appears in the above-identified patent and that said Letters Patent is hereby corrected as shown below:

Col. 1, line 18, after "column," insert

-- between the patient's blood vessel and the transducer --

Column 1, line 19, after "communicated," insert

-- to the transducer so that the patient's blood pressure --

Column 6, line 7, "to" should be -- into --

Signed and Sealed this

Ninth Day of March, 1993

Attest:

STEPHEN G. KUNIN

Attesting Officer

Acting Commissioner of Patents and Trademarks